United States Patent [19]

Aoyama et al.

[11] Patent Number: 5,393,386
[45] Date of Patent: Feb. 28, 1995

[54] METHOD FOR PREPARING AQUEOUS QUATERNARY AMMONIUM HYDROXIDE SOLUTION

[75] Inventors: Tetsuo Aoyama; Toshio Kondo; Yasushi Sugawara; Masahiro Miyake, all of Niigata, Japan

[73] Assignee: Mitsubishi Gas Chemical Company, Inc., Tokyo, Japan

[21] Appl. No.: 168,049

[22] Filed: Dec. 15, 1993

[30] Foreign Application Priority Data

Dec. 28, 1992 [JP] Japan .................................. 4-348756
May 21, 1993 [JP] Japan .................................. 5-120173

[51] Int. Cl.$^6$ .............................................. C25B 3/02
[52] U.S. Cl. .................................... 204/78; 204/84; 204/182.4
[58] Field of Search .................. 204/59 R, 72, 78, 83, 204/84, 182.4, 91, 182.3

[56] References Cited

U.S. PATENT DOCUMENTS

4,572,769  2/1986  Shimizu ................................ 204/72
4,634,509  1/1987  Shimizu et al. .................... 204/182.4

FOREIGN PATENT DOCUMENTS

0255756  2/1988  European Pat. Off. .
0269949  6/1988  European Pat. Off. .

OTHER PUBLICATIONS

Database WPI, Derwent Publications Ltd., London, GB; AN 88-068532 of JP-A-60 165 469 Jul. 16, 1986.

*Primary Examiner*—John Niebling
*Assistant Examiner*—Edna Wong
*Attorney, Agent, or Firm*—Frishauf, Holtz, Goodman & Woodward

[57] ABSTRACT

The present invention-provides a method for preparing a high-purity aqueous quaternary ammonium hydroxide solution, and there is here disclosed this method for preparing the high-purity aqueous quaternary ammonium hydroxide solution which comprises reacting a quaternary ammonium organic acid salt with hydrogen peroxide, oxygen or an oxygen-containing gas in the presence of a platinum group metal catalyst to produce a quaternary ammonium inorganic acid salt, and then electrolyzing this inorganic acid salt by the use of an electrolytic tank having a cation exchange membrane.

18 Claims, No Drawings

METHOD FOR PREPARING AQUEOUS QUATERNARY AMMONIUM HYDROXIDE SOLUTION

BACKGROUND OF THE INVENTION (1) Field of the Invention

The present invention relates to a method for preparing a high-purity aqueous quaternary ammonium hydroxide solution.

More specifically, it relates to a method for preparing a high-purity aqueous quaternary ammonium hydroxide solution which comprises reacting a quaternary ammonium organic acid salt with hydrogen peroxide, oxygen or an oxygen-containing gas to produce a quaternary ammonium inorganic acid salt, and then electrolyzing the inorganic acid salt.

(2) Description of the Related Arts

A high-purity aqueous quaternary ammonium hydroxide solution has been used in a wide application range, and for example, it has been utilized as a developing agent for resists in a manufacturing process of LSIs and LCDs, a washing agent for semiconductor substrates, and the like.

Heretofore, as techniques for preparing an aqueous quaternary ammonium hydroxide solution, the following methods are known:

(a) A preparation method which comprises electrolyzing a quaternary ammonium halide obtained by reacting a trialkylamine with an alkyl halide, (b) a preparation method which comprises electrolyzing a quaternary ammonium organic carboxylic acid salt obtained by reacting a trialkylamine with an organic carboxylate (Japanese Patent Application Laid-open No. 100690/1985), (c) a preparation method which comprises electrolyzing a quaternary ammonium inorganic acid salt obtained by reacting a trialkylamine with a dialkyl carbonate (Japanese Patent Application Laid-open No. 170588/1986 and U.S. Pat. No. 4,634,509), and the like.

However, in the above-mentioned preparation method (a), halogen ions and a halogen gas which are harmful and corrosive are formed at high concentrations in an anode chamber in an electrolysis step, so that some troubles take place, and for example, an anode itself and a device such as an electrolytic tank are corroded. In addition, part of the halogen ions present in the anode chamber pass through a cation exchange membrane and transfer to a cathode chamber at the time of the electrolysis, or the product is contaminated with impurities as a result of the above-mentioned corrosion sometimes, so that the purity of the aqueous quaternary ammonium hydroxide solution produced in the cathode chamber tends to deteriorate. For these reasons, the above-mentioned preparation process (a) is not preferable as the method for preparing the high-purity aqueous quaternary ammonium hydroxide solution.

On the other hand, in the above-mentioned method (b), corrosive organic acid ions such as formic acid ions are formed in the electrolysis step, and the anode itself and a device such as an electrolytic tank are liable to be corroded. As measures against the corrosion, it has been tried to electrolytically oxidize the carboxylic acid ions into a harmless carbon dioxide gas, but in this process, a large amount of electrical energy is inconveniently required. In the case of the electrolysis method using the cation exchange membrane, part of the organic acid ions pass through the ion exchange membrane and transfer into a cathode chamber, or the product is contaminated with impurities as a result of the above-mentioned corrosion sometimes, and also in this case, the purity of the aqueous quaternary ammonium hydroxide solution produced in the cathode chamber tends to deteriorate. In consequence, the above-mentioned preparation process (b) is not preferable as the method for preparing the high-purity aqueous quaternary ammonium hydroxide solution.

In addition, the above-mentioned preparation method (c) is a technique which comprises electrolyzing a quaternary ammonium inorganic acid salt obtained by using, as a raw material, a dialkyl carbonate prepared from phosgene and an alcohol. However, a chlorine compound derived from phosgene tends to be mixed with the above-mentioned raw material dialkyl carbonate, so that the aqueous quaternary ammonium hydroxide solution was contaminated, which often disturbs the manufacture of the desired high-purity aqueous quaternary ammonium hydroxide solution. In addition, the manufacturing cost of the dialkyl carbonate as the raw material is high in the case of a present technique, and therefore this method is not always suitable to prepare the inexpensive aqueous quaternary ammonium hydroxide solution.

As understood from the foregoing, the already known various methods for preparing the high-purity aqueous quaternary ammonium hydroxide solution have many problems, and thus it has been desired to develop a method for preparing the high-purity aqueous quaternary ammonium hydroxide solution at a low cost.

SUMMARY OF THE INVENTION

An object of the present invention is to provide a method for preparing a high-purity aqueous quaternary ammonium hydroxide solution at a low cost.

The present invention is directed to a novel method for preparing an aqueous quaternary ammonium hydroxide solution which comprises the steps of reacting an aqueous solution of a quaternary ammonium organic acid salt with hydrogen peroxide, oxygen or an oxygen-containing gas to synthesize a quaternary ammonium inorganic acid salt, and then electrolyzing the synthesized quaternary ammonium inorganic acid salt.

More specifically, the present invention is directed to a method for preparing a high-purity aqueous quaternary ammonium hydroxide solution which comprises the steps of reacting an aqueous solution of a quaternary ammonium organic acid salt with hydrogen peroxide, oxygen or an oxygen-containing gas preferably at 10° to 200° C. in the presence of a catalyst of a platinum group metal such as palladium or platinum to obtain a quaternary ammonium inorganic acid salt, and then electrolyzing the aqueous solution of the synthesized quaternary ammonium inorganic acid salt.

DETAILED DESCRIPTION OF THE INVENTION

A quaternary ammonium organic acid salt which can be used in the present invention can be represented by the formula (1)

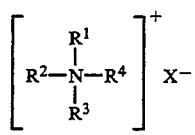

(wherein each of $R^1$ to $R^4$ is an alkyl group having 1 to 3 carbon atoms, and they may be mutually identical or different; and X is an organic acid radical).

Typical examples of the quaternary ammonium organic acid salt represented by the above-mentioned formula include tetramethylammonium formate, tetramethylammonium acetate, tetramethylammonium propionate, tetramethylammonium oxalate, tetramethylammonium malonate, tetramethylammonium maleate, tetramethylammonium succinate, tetramethylammonium fumarate, tetramethylammonium acrylate, tetramethylammonium methacrylate, tetramethylammonium benzoate, tetraethylammonium formate, tetraethylammonium acetate, tetraethylammonium propionate, tetraethylammonium oxalate, trimethylethylammonium formate, trimethylethylammonium acetate, tetrapropylammonium formate, tetrapropylammonium acetate and the like. Above all, tetramethylammonium formate and tetraethylammonium formate are preferable.

The quaternary ammonium organic acid salt represented by the above-mentioned formula can be obtained in a known manner from, for example, a trialkylamine and an organic acid ester, for example, an aliphatic monocarboxylate such as a formate, an acetate or a propionate, a polycarboxylate such as an oxalate, a malonate, a maleate, a succinate and a fumarate, and an unsaturated organic acid ester such as an acrylate.

Hydrogen peroxide which can be used in the present invention is preferably used in the state of an aqueous solution.

Oxygen which can be used in the present invention means a gas containing oxygen as the main component, but this gas may contain small amounts of other gaseous components. In the reaction with the quaternary ammonium organic acid salt, the presence of an inert gas does not cause any problem, and thus high-purity oxygen is not required. In general, oxygen is blown in the form of a gas into the reaction system.

The oxygen-containing gas which can be used in the present invention is not a gas particularly containing oxygen as the main component, and by this point, the oxygen-containing gas can be distinguished from the above-mentioned oxygen. However, the component to be used in the oxygen-containing gas is oxygen, and so it is meaningless to clearly distinguish both the materials. A typical example of the oxygen-containing gas is air, but needless to say, components other than oxygen in the oxygen-containing gas are required to be inert in the reaction system, as described in the above-mentioned paragraph regarding oxygen. With regard to the purity of the oxygen-containing gas, the above-mentioned description of oxygen can also be applied. Another example of the oxygen-containing gas is a mixed gas of oxygen and an inert gas such as nitrogen, a carbon dioxide gas, argon or helium.

As a catalyst which can be used in the reaction of the quaternary ammonium organic acid salt and hydrogen peroxide, oxygen or oxygen-containing gas in the present invention, there can be used at least one of platinum group metals consisting of palladium, platinum, ruthenium, rhodium and iridium. No particular restriction is put on a morphology, pretreatment conditions and the like of the platinum group metal to be used.

The catalyst itself may be used in a highly active state such as powder, but it is most effective to use the same in the form of a usually utilizable supported catalyst. Thus, the catalyst, when used, can be supported on a carbon-based carrier such as active carbon, carbon fiber or active carbon fiber, or an inorganic carrier such as silica, alumina, silica-alumina or zeolite. Above all, a catalyst in which palladium is supported on the carbon-based carrier is particularly preferable.

In the supported catalyst which can be used in the present invention, the amount of a metal to be supported such as palladium, platinum, ruthenium, rhodium or iridium is preferably in the range of from 0.01 to 20% by weight, more preferably from 0.05 to 10% by weight with respect to the weight of the carrier.

A molar ratio of the quaternary ammonium organic acid to hydrogen peroxide, oxygen or oxygen-containing gas in the preparation method of the present invention is preferably such that the quaternary ammonium organic acid salt:hydrogen peroxide, oxygen or oxygen in the oxygen-containing gas is 1:0.5 or more. In this case, the typical molar ratio of hydrogen peroxide or the like can be suitably selected in consideration of the kind of quaternary ammonium organic acid salt, the kind of catalyst, reaction conditions and the like, but in general, the molar ratio is preferably in the range of from 0.5 to 100, more preferably from 0.5 to 50, and in the case of hydrogen peroxide, it is preferably in the range of from 1 to 20, more preferably from 1 to 10.

In the present invention, the temperature of the reaction between the quaternary ammonium organic acid salt and hydrogen peroxide, oxygen or the oxygen-containing gas in the presence of the platinum group metal catalyst is preferably in the range of from 10° to 200° C. more preferably from 20° to 150° C.

In the present invention, the reaction between the quaternary ammonium organic acid salt and hydrogen peroxide, oxygen or the oxygen-containing gas can be carried out under atmospheric pressure or an elevated pressure. Furthermore, the reaction can be done by any of a batch system, a semi-batch system and a continuous system. When the quaternary ammonium organic acid salt is reacted with hydrogen peroxide, oxygen or the oxygen-containing gas, the quaternary ammonium inorganic acid salt is obtained in the form of an aqueous solution, and then forwarded to an electrolysis step, in which the aqueous solution of the quaternary ammonium inorganic acid salt is subjected to an electrolysis reaction.

As an electrolytic tank, a single tank system is not preferable, because the quaternary ammonium inorganic acid salt of the raw material and the quaternary ammonium hydroxide of the electrolysis product are present in a mixing state in the single tank and the separation of the high-purity electrolysis product is complicated and difficult. Therefore, the electrolytic tank which can be suitably used is usually compartmentalized into an anode chamber having an anode and a cathode chamber having a cathode by a diaphragm made of a cation exchange membrane. If necessary, a multi-chamber electrolytic tank having one or more intermediate chambers compartmented by disposing a plurality of the cation exchange membranes at a predetermined interval can also be used.

In the case that the cation exchange membrane is used in the present invention, as a material for the membrane, there can be used an anti-corrosive fluororesin having a cation exchange group such as a sulfonic acid group or a carboxylic acid group, and in addition thereto, a styrenedivinylbenzene copolymer having the above-mentioned ion exchange group can also be used.

In the present invention, as the anode which can be used in the electrolytic tank, there can be employed an electrode suitable for this kind of electrolysis, for example, a high-purity carbon electrode or a titanium electrode covered with an oxide of a platinum group metal such as platinum or iridium. Furthermore, as the cathode, there can be used an electrode suitable for this kind of electrolysis, for example, stainless steel or nickel. The anode and cathode can be used in any form of a plate, a net, a porous plate and the like.

In this electrolysis, either of a batch system and a continuous system can be employed, but the concentration of the quaternary ammonium inorganic acid salt of the raw material for the electrolysis which is fed to the anode chamber is preferably adjusted to 1–60% by weight, more preferably 3–40% by weight. Furthermore, to the cathode chamber, water is usually fed, but when water is singly used, electrical conductivity is so low that the electrolysis is difficult to occur at the start of the operation. Hence, it is desirable to use water containing a small amount, e.g., 0.01 to 5% by weight of quaternary ammonium hydroxide which is the end product.

The electrolysis can be carried out by applying direct-current voltage, and its current density is preferably in the range of from 1 to 100 A/dm$^2$, more preferably from 3 to 50 A/dm$^2$. The temperature of an electrolyte is preferably in the range of from 10° to 50° C. Moreover, it is desirable that during the electrolysis, the atmosphere on the surface of the electrolyte is made up of an inert gas such as nitrogen or argon.

Next, the present invention will be described in detail in reference with examples, but the scope of the present invention should not be limited to these examples.

EXAMPLE 1

A reactor having an inner diameter of 40 mm was filled with one liter of a catalyst obtained by supporting palladium on active carbon having a particle diameter of from 1 to 2 mm, the amount of palladium to be supported being 0.5% by weight based on the weight of the active carbon. Afterward, an aqueous solution containing 20.6% by weight of tetramethylammonium formate and 7.5% by weight of hydrogen peroxide were fed to the reactor heated up to 60° C. at a flow rate of 1,000 g/hr under atmospheric pressure.

After reaction, the concentration of the resulting tetramethylammonium inorganic acid salt in the aqueous solution was 23.3% by weight and that of tetramethylammonium formate was 0.02% by weight, and any hydrogen peroxide was not detected. This aqueous solution was then directly used for subsequent electrolysis.

In an electrolytic tank, a fluorine-based cation exchange membrane (trade name Nafion 324, made by Du Pont) was used as a cation exchange membrane, and the electrolytic tank was compartmentalized into an anode chamber and a cathode chamber with this membrane. A titanium electrode covered with platinum was used as an anode, and a nickel electrode was used as a cathode. The aqueous solution of the tetramethylammonium inorganic acid salt and a 0.5 wt % aqueous tetramethylammonium hydroxide solution were circulated through an anode chamber and a cathode chamber, respectively, and the electrolysis was carried out at an electrolyte temperature of 35° C. by applying a direct current of 10 A/dm$^2$. As a result, 16.2% by weight of the aqueous tetramethylammonium hydroxide solution was obtained in the cathode chamber at an electrolytic voltage of from 5 to 6 V at an average current efficiency of 88%. After the electrolysis, the concentration of tetramethylammonium formate in the aqueous tetramethylammonium hydroxide solution was 0.003% by weight.

EXAMPLE 2

The same reactor as in Example 1 was filled with the same catalyst under the same conditions as in Example 1, and an aqueous solution containing 28.8% by weight of tetramethylammonium formate and 9.0% by weight of hydrogen peroxide were fed to the reactor heated up to 40° C. at a flow rate of 500 g/hr under atmospheric pressure.

After reaction, the concentration of the resulting tetramethylammonium inorganic acid salt in the aqueous solution was 32.5% by weight and that of tetramethylammonium formate was 0.05% by weight, and no hydrogen peroxide was detected. This aqueous solution was then directly used for subsequent electrolysis.

There was used the same electrolytic tank as in Example 1 except that a titanium electrode covered with iridium oxide was used as an anode. The aqueous solution of the tetramethylammonium inorganic acid salt and the like and a 0.3 wt % aqueous tetramethylammonium hydroxide solution were circulated through an anode chamber and a cathode chamber, respectively, and the electrolysis was carried out at an electrolyte temperature of 40° C. by applying a direct current of 15 A/dm$^2$. As a result, 20.7% by weight of the aqueous tetramethylammonium hydroxide solution was obtained in the cathode chamber at an electrolytic voltage of from 7 to 9 V at an average current efficiency of 84%. In this case, the concentration of tetramethylammonium formate in the thus obtained aqueous tetramethylammonium hydroxide solution was 0.007% by weight.

EXAMPLE 3

The same reactor as in Example 1 was filled with one liter of a catalyst obtained by supporting palladium on silica having a particle diameter of from 1 to 2 mm, the amount of palladium to be supported being 1.0% by weight based on the weight of the silica. Afterward, an aqueous solution containing 8.3% by weight of tetramethylammonium formate and 6.0% by weight of hydrogen peroxide were fed to the reactor heated up to 50° C. at a flow rate of 300 g/hr under atmospheric pressure.

After reaction, the concentration of the resulting tetramethylammonium inorganic acid salt in the aqueous solution was 9.1% by weight and that of tetramethylammonium formate was 0.21% by weight, and no hydrogen peroxide was detected. This aqueous solution was then directly used for subsequent electrolysis.

The same electrolytic tank as in Example 2 was used, and the aqueous solution of the tetramethylammonium inorganic acid salt and the like and a 0.5 wt % aqueous tetramethylammonium hydroxide solution were circulated through an anode chamber and a cathode chamber, respectively, and the electrolysis was carried out at an electrolyte temperature of 40° C. by applying a direct current of 20 A/dm$^2$. As a result, 7.8% by weight of the aqueous tetramethylammonium hydroxide solution was obtained in the cathode chamber at electrolytic voltage of from 8 to 12 V at an average current efficiency of 81%. In this case, the concentration of tetramethylammonium formate in the thus obtained aqueous tetramethylammonium hydroxide solution was 0.012% by weight.

EXAMPLE 4

The same reactor as in Example 1 was filled with one liter of a catalyst obtained by supporting palladium on active carbon having a particle diameter of from 1 to 2 mm, the amount of palladium to be supported being 0.5% by weight based on the weight of the active carbon. Afterward, the reactor was heated up to 80° C., and an aqueous solution containing 20.6% by weight of tetramethylammonium formate was then fed to the reactor at a flow rate of 300 g/hr under atmospheric pressure, while an oxygen gas was simultaneously fed at a flow rate of 200 l/hr.

After reaction, the concentration of the resulting tetramethylammonium inorganic acid salt in the aqueous solution was 22.9% by weight and that of tetramethylammonium formate was 0.081% by weight. This aqueous solution was then directly used for subsequent electrolysis.

In an electrolytic tank, a fluorine-based cation exchange membrane (trade name Nafion 324, made by Du Pont) was used as a cation exchange membrane, and the electrolytic tank was compartmentalized into an anode chamber and a cathode chamber with this membrane. A titanium electrode covered with platinum was used as an anode, and a nickel electrode was used as a cathode. The aqueous solution of the tetramethylammonium inorganic acid salt and the like and a 0.5 wt % aqueous tetramethylammonium hydroxide solution were circulated through an anode chamber and a cathode chamber, respectively, and the electrolysis was carried out at an electrolyte temperature of 35° C. by applying a direct current of 10 A/dm$^2$. As a result, 17.0% by weight of the aqueous tetramethylammonium hydroxide solution was obtained in the cathode chamber at an electrolytic voltage of from 5 to 6 V at an average current efficiency of 88%. In this case, the concentration of tetramethylammonium formate in the thus obtained aqueous tetramethylammonium hydroxide solution was 0.002% by weight.

EXAMPLE 5

The same reactor as in Example 4 filled with the same catalyst as in Example 4 was heated up to 60° C. and an aqueous solution containing 10.1% by weight of tetramethylammonium formate was fed to the reactor at a flow rate of 400 g/hr under atmospheric pressure, while air was fed thereto at a flow rate of 460 l/hr.

After reaction, the concentration of the resulting tetramethylammonium inorganic acid salt in the aqueous solution was 11.1% by weight and that of tetramethylammonium formate was 0.03% by weight. This aqueous solution was then directly used for subsequent electrolysis.

There was used the same electrolytic tank as in Example 1 except that a titanium electrode covered with iridium oxide was used as an anode. The aqueous solution of the tetramethylammonium inorganic acid salt and the like and a 0.3 wt % aqueous tetramethylammonium hydroxide solution were circulated through an anode chamber and a cathode chamber, respectively, and the electrolysis was carried out at an electrolyte temperature of 40° C. by applying a direct current of 15 A/dm$^2$. As a result, 21.9% by weight of the aqueous tetramethylammonium hydroxide solution was obtained in the cathode chamber at an electrolytic voltage of from 7 to 9 V at an average current efficiency of 84%. In this case, the concentration of tetramethylammonium formate in the thus obtained aqueous tetramethylammonium hydroxide solution was 0.002% by weight.

EXAMPLE 6

The same procedure as in Example 1 was carried out except for the use of a catalyst obtained by supporting platinum on active carbon having a particle diameter of from 1 to 2 mm, the amount of platinum to be supported being 0.5% by weight based on the weight of the active carbon, and a reactor was then heated up to 50° C. Afterward, an aqueous solution containing 9.5% by weight of tetramethylammonium formate was fed to the reactor at a flow rate of 200 g/hr under atmospheric pressure, while oxygen was fed at a flow rate of 500 l/hr.

After reaction, the concentration of the resulting tetramethylammonium inorganic acid salt was 10.2% by weight and that of tetramethylammonium formate was 0.005% by weight. This aqueous solution was then directly used for subsequent electrolysis.

The same electrolytic tank as in Example 5 was used, and the aqueous solution of the tetramethylammonium inorganic acid salt and the like and a 0.5 wt % aqueous tetramethylammonium hydroxide solution were circulated through an anode chamber and a cathode chamber, respectively, and the electrolysis was carried out at an electrolyte temperature of 40° C. by applying a direct current of 20 A/dm$^2$. As a result, 8.2% by weight of the aqueous tetramethylammonium hydroxide solution was obtained in the cathode chamber at an electrolytic voltage of from 8 to 12 V at an average current efficiency of 81%. In this case, the concentration of tetramethylammonium formate in the thus obtained aqueous tetramethylammonium hydroxide solution was 0.0001% by weight or less.

EXAMPLE 7

Reaction was carried out under the same conditions as in Example 4 except that reaction pressure was 8 kg/cm$^2$.

After reaction, the concentration of the resulting tetramethylammonium inorganic acid salt was 23.0% by weight and that of tetramethylammonium formate was 0.01% by weight. This aqueous solution was then directly used for electrolysis.

The same electrolytic tank as in Example 5 was used, and the aqueous solution of the tetramethylammonium inorganic acid salt and the like and a 0.5 wt % aqueous tetramethylammonium hydroxide solution were circulated through an anode chamber and a cathode chamber, respectively, and the electrolysis was carried out at an electrolyte temperature of 35° C. by applying a direct current of 10 A/dm$^2$. As a result, 17.9% by weight of the aqueous tetramethylammonium hydroxide solution was obtained in the cathode chamber at an electrolytic voltage of from 5 to 6 V at an average current efficiency of 89%. In this case, the concentration of tetramethylammonium formate in the thus obtained aqueous tetramethylammonium hydroxide solution was 0.0001% by weight or less.

EXAMPLE 8

The same reactor as in Example 4 filled with the same catalyst as in Example 4 was heated up to 50° C., and an aqueous solution containing 14.0% by weight of tetraethylammonium formate was fed to the reactor at a flow rate of 200 g/hr under atmospheric pressure, while an oxygen gas was fed thereto at a flow rate of 200 l/hr. After reaction, the concentration of the resulting tetraethylammonium inorganic acid salt was 14.7% by weight and that of tetraethylammonium formate was 0.01% by weight.

Next, the same electrolytic tank as in Example 1 was used, and the aqueous solution of the tetraethylammonium inorganic acid salt and the like and a 0.5 wt % aqueous tetraethylammonium hydroxide solution were circulated through an anode chamber and a cathode chamber, respectively, and the electrolysis was carried out at an electrolyte temperature of 40° C. by applying a direct current of 20 A/dm$^2$. As a result, 12.8% by weight of the aqueous tetraethylammonium hydroxide solution was obtained in the cathode chamber at an electrolytic voltage of from 10 to 14 V at an average current efficiency of 75%. In this case, the concentration of tetraethylammonium formate in the thus obtained aqueous tetraethylammonium hydroxide solution was 0.008% by weight or less.

What is claimed is:

1. A method for preparing an aqueous quaternary ammonium hydroxide solution which comprises the steps of reacting an aqueous solution of a quaternary ammonium organic acid salt represented by the formula (1)

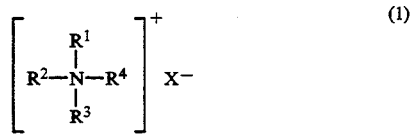

(1)

wherein each of R$^1$ to R$^4$ is an alkyl group having 1 to 3 carbon atoms, and R$^1$ to R$^4$ are mutually identical or different; and X is an organic acid radical, with hydrogen peroxide, oxygen or an oxygen-containing gas in the presence of a platinum group metal catalyst to obtain a quaternary ammonium inorganic acid salt, and then electrolyzing the aqueous solution of the quaternary ammonium inorganic acid salt.

2. The method for preparing an aqueous quaternary ammonium hydroxide solution according to claim 1 wherein the quaternary ammonium organic acid salt is tetramethylammonium formate or tetraethylammonium formate.

3. The method for preparing an aqueous quaternary ammonium hydroxide solution according to claim 1 wherein a molar ratio of the quaternary ammonium organic acid salt to hydrogen peroxide, oxygen or oxygen in the oxygen-containing gas is 0.5 to 100.

4. The method for preparing an aqueous quaternary ammonium hydroxide solution according to claim 3 wherein the reacting is carried out with hydrogen peroxide, and a molar ratio of the quaternary ammonium organic acid salt to the hydrogen peroxide being 1 to 20.

5. The method for preparing an aqueous quaternary ammonium hydroxide solution according to claim 1 wherein the platinum group metal of the platinum group metal catalyst is at least one selected from the group consisting of palladium, platinum, ruthenium, rhodium and iridium.

6. The method for preparing an aqueous quaternary ammonium hydroxide solution according to claim 1 wherein the platinum group metal catalyst is a catalyst in which a platinum group metal is supported on a carrier, the amount of the platinum group metal supported being 0.01 to 20% by weight with respect to the weight of the carrier.

7. The method for preparing an aqueous quaternary ammonium hydroxide solution according to claim 6 wherein the carrier is selected from the group consisting of carbon carriers selected from the group consisting of active carbon and carbon fiber and inorganic carriers selected from the group consisting of silica, alumina and silica-alumina.

8. The method for preparing an aqueous quaternary ammonium hydroxide solution according to claim 1 wherein the aqueous quaternary ammonium inorganic acid salt solution is fed to an anode chamber during the electrolysis at a concentration of 1 to 60% by weight.

9. The method for preparing an aqueous quaternary ammonium hydroxide solution according to claim 1 wherein the reacting of the quaternary ammonium inorganic acid salt is carried out at a temperature of 10° to 200° C.

10. The method for preparing an aqueous quaternary ammonium hydroxide solution according to claim 6 wherein the carrier is an active carbon fiber.

11. The method for preparing a aqueous quaternary ammonium hydroxide solution according to claim 6 wherein the carrier is a zeolite.

12. The method of preparing an aqueous quaternary ammonium hydroxide solution according to claim 3 wherein the quaternary ammonium organic acid salt is selected from the group consisting of tetramethylammonium formate, tetramethylammonium acetate, tetramethylammonium propionate, tetramethylammonium oxalate, tetramethylammonium malonate, tetramethylammoniummaleate, tetramethylammonium succinate, tetramethylammonium fumarate, tetramethylammonium acrylate, tetramethylammonium methacrylate, tetramethylammonium benzoate, tetraethylammonium formate, tetraethylammonium acetate, tetraethylammonium propionate, tetraethylammonium oxalate, trimethylethylammonium formate, trimethylethylammonium acetate, tetrapropylammonium formate and tetrapropylammonium acetate.

13. The method for preparing an aqueous quaternary ammonium hydroxide solution according to claim 12 wherein the platinum group metal of the platinum group metal catalyst is selected from the group consisting of palladium, platinum, ruthenium, rhodium and iridium; the platinum group metal being supported on a carrier selected from the group consisting of active carbon, carbon fibers, silica, alumina and silica-alumina; and the platinum group metal being in an amount of 0.05 to 10% by weight based on the weight of the carrier.

14. The method for preparing an aqueous quaternary ammonium hydroxide solution according to claim 13 wherein the reacting is carried out at a temperature of 20° to 150° C.

15. The method for preparing an aqueous quaternary ammonium hydroxide solution according to claim 14 wherein the electrolyzing is carried out with an electrolyte in an electrolytic tank having an anode chamber and a cathode chamber and the aqueous quaternary ammonium inorganic acid salt solution being fed to the anode chamber at a concentration of 3 to 40% by weight.

16. The method for preparing an aqueous quaternary ammonium hydroxide solution according to claim 15 wherein the electrolyzing is carried out at a current density of 1 to 100 A/dm$^2$ and the electrolyte is at a temperature of 10° to 50° C.

17. The method for preparing an aqueous quaternary ammonium hydroxide solution according to claim 16 wherein the current density is 3 to 50 A/dm$^2$.

18. The method for preparing an aqueous quaternary ammonium hydroxide solution according to claim 17 wherein the quaternary ammonium organic acid salt is tetramethylammonium formate or tetraethylammonium formate.

* * * * *